United States Patent
Lord et al.

(10) Patent No.: US 10,271,545 B2
(45) Date of Patent: Apr. 30, 2019

(54) ANTIMICROBIAL COMPOSITIONS

(71) Applicant: Cosilion LLC, Racine, WI (US)

(72) Inventors: Jeffrey M. Lord, Racine, WI (US);
Tom Tinerella, Racine, WI (US);
Robert C. Parker, Racine, WI (US)

(73) Assignee: Agent Plus Solutions LLC, Germantown, WI (US)

( * ) Notice: Subject to any disclaimer, the term of this patent is extended or adjusted under 35 U.S.C. 154(b) by 290 days.

(21) Appl. No.: 15/043,762

(22) Filed: Feb. 15, 2016

(65) Prior Publication Data

US 2016/0242411 A1     Aug. 25, 2016

Related U.S. Application Data

(63) Continuation of application No. 13/757,793, filed on Feb. 2, 2013.

(51) Int. Cl.
| | | |
|---|---|---|
| *A01N 25/04* | (2006.01) | |
| *A01N 25/24* | (2006.01) | |
| *A01N 25/10* | (2006.01) | |
| *A01N 59/16* | (2006.01) | |
| *A01N 59/20* | (2006.01) | |

(52) U.S. Cl.
CPC ............ *A01N 25/24* (2013.01); *A01N 25/04* (2013.01); *A01N 25/10* (2013.01); *A01N 59/16* (2013.01); *A01N 59/20* (2013.01); *Y10T 428/249921* (2015.04)

(58) Field of Classification Search
None
See application file for complete search history.

(56) References Cited

U.S. PATENT DOCUMENTS

| | | |
|---|---|---|
| 6,287,285 B1 | 9/2001 | Michal et al. |
| 7,357,949 B2 | 4/2008 | Trogolo et al. |
| 7,951,761 B2 | 5/2011 | Gonzalez |
| 8,361,553 B2 | 1/2013 | Karandikar et al. |
| 8,425,926 B2 | 4/2013 | Qiu et al. |
| 8,709,394 B2 | 4/2014 | Chisholm et al. |
| 2009/0123507 A1 | 5/2009 | Ohrlein et al. |
| 2010/0120311 A1 | 5/2010 | Bender et al. |
| 2010/0234263 A1 | 9/2010 | Wasan et al. |
| 2010/0234363 A1 | 9/2010 | Itai et al. |
| 2011/0236441 A1 | 9/2011 | Ohrlander et al. |
| 2013/0122321 A1 | 5/2013 | Karandikar et al. |
| 2013/0177504 A1 | 7/2013 | Macoviak |
| 2013/0228943 A1 | 9/2013 | Qiu et al. |
| 2013/0315972 A1 | 11/2013 | Krasnow et al. |
| 2014/0079805 A1 | 3/2014 | Addison et al. |
| 2014/0170238 A1 | 6/2014 | Cliff et al. |

OTHER PUBLICATIONS

Alexandra Pica, Denisa Ficai, Cornelia Guran: In-Situe Synthesis of Nano Silver Particles Used in Obtaining of Antimicrobial Film-Forming Materials. Rev. Chim. (Bucharest) vol. 63:5 (2012) pp. 459-462.
P. Kaali, M.M. Perez-Madrigal, E Stromberg, R.E. Aune, Gy Czel, S Karlsson. The Influence of Ag+, Zn+ and Cu2+ Exchanged Zeolite on Antimicrobial and Long Term In Vitro Stability of Medical Grade Polyether Polyurethane; eXPRESS Polymer Letters vol. 5 No. 12 (2011) 1028-1040.
Robert Prucek, Jiri Tucek, Martina Kilianova, Ales Panacek, Libor Kvitek, Jan Filip, Milan Kolar, Katerina Tomankova, Radek Zboril. The Targeted Antibacterial and Antifungal Properties of Magnetic Nanocomposite of Iron Oxide and Silver Nanoparticles; Biomaterials 32 (2011) 4704-4713.
Taeho Kim, Seungwoong Nam, Soonho Lim & Heesuk Kim. Facile In-Situ Preparation of Poly(Acrylic Acid)-Silver Nanocomposite Thin Films with Highly Dispersed Silver Nanoparticles; Mol. Cryst. Liq.Cryst., vol. 568:1, pp. 170-178, 2012.
V. Melinte, T. Buriana, I.D. Moraru, E.G. Buriana. Silver-Polymer Composite Materials With Antibacterial Properties; Digest Journal of Nanomaterials and Biostructures, vol. 6: 1, Jan.-Mar. 2011, pp. 213-223.
Yu-Sen E. Lin, Radisav D. Vidic, Janet E. Stout, Victor L. Yu. Individual and Combined Effects of Copper and Silver Ions on Inactivation of Legionella Pneumophila; Wat. Res. vol. 30, No. 8 pp. 1905-1913 (1996).

*Primary Examiner* — Nannette Holloman
(74) *Attorney, Agent, or Firm* — Meunier Carlin & Curfman LLC

(57) ABSTRACT

A surface treatment composition includes a surface treatment agent and an antimicrobial mixture comprising oxidizable antimicrobial particles distributed throughout a film-forming agent.

32 Claims, 1 Drawing Sheet

ANTIMICROBIAL COMPOSITIONS

CROSS-REFERENCE TO RELATED APPLICATION

This application is a continuation of U.S. application Ser. No. 13/757,793, entitled, "ANTIMICROBIAL COMPOSITIONS," filed Feb. 23, 2013, the disclosures of which are expressly incorporated herein by reference in their entireties.

FIELD OF INVENTION

The present invention relates generally to antimicrobial compositions and more particularly to a surface treatment composition comprising oxidizable antimicrobial particles.

BACKGROUND OF THE INVENTION

Application of cleaning agents to surfaces to clean soil and stains is well known. Research dealing with exploring how antimicrobial and antifungal agents may be incorporated into cleaning agents for improving their ability to control disease-causing bacteria has also been conducted.

A number of inorganic materials have been shown to exhibit antimicrobial and/or antifungal properties. For example, metals such as silver, copper, zinc, mercury, tin, lead, bismuth, cadmium, chromium and thallium, have been shown to exhibit such properties. While the reasons for this are not yet fully understood, it is thought that ionized forms of these metals interact with thiol containing proteins and DNA thereby preventing the normal biological functions of bacterial or fungal cells.

United States Patent Application Publication No. 20130234263 to Wasan et al. discloses nano-fluids as cleaning compositions for cleaning soiled surfaces, and a method and formulation for their use. The disclosure describes nano-fluids comprising aqueous suspensions of hydrophilic nanoparticles or polymers, useful in soil removal from hard, semi-hard or soft surfaces, and particularly for improved removal of grass and grease stains.

U.S. Pat. No. 7,081,441 to McDonald et al. discloses a composition for cleaning and/or treating surfaces. The composition comprises a nanoparticles component selected from the group consisting of metal oxyhydroxides, modified metal oxyhydroxides and mixtures thereof; a buffer/modifier component; optionally an adjunct ingredient, and the balance of the composition being a polar solvent. According to the disclosure, the metal oxyhydrides in aqueous solution are converted into and maintained as nanoparticulate sized modified metal oxyhydroxides. In one aspect, a dry film results from contacting a surface with the composition that comprises greater than or equal to about 0.05 µg of nanoparticles per cm' of treated surface.

In the publication entitled "Facile In-Situ Preparation of Poly(Acrylic Acid)-Silver Nanocomposite Thin Films with Highly Dispersed Silver Nanoparticles" (Kim et al.) Mol. Cryst. Liq. Cryst. Vol 568: pp 170-178, 2012, there is disclosed a method of preparing of PAA-Ag nanocomposite thin films with highly dispersed Ag nanoparticles. During the method, silver salts are chemically reacted with acrylic acid, and as a result silver nanoparticles are produced in situ within an acrylic film.

In the publication entitled "In-situ Synthesis of Nano Silver Particles Used in Obtaining of Antimicrobial Film-Forming Materials" (Pica et al.) REV. CHEM. (Bucharest) 63, No. 5, 2012, there is disclosed processes by which silver nanoparticles that are stable in time are obtained for use in formulating antimicrobial coating materials. Chemical synthesis of the silver nanoparticles comprises dissolving and reducing metals salts in a polymer matrix.

U.S. Pat. No. 7,357,949 to Trogolo et al. discloses an encapsulated inorganic antimicrobial additive for controlled release. Microcapsules comprising an antimicrobial agent are encapsulated within a hydrophilic polymer, which is capable of absorbing sufficient water as to enable the action of the encapsulated antimicrobial agent. In this patent, the antimicrobial agent is a zeolite that retains metal ions until they are able to be released via ion exchange.

While it is known to provide surface cleaning compositions that incorporate antimicrobial agents, improvements for prolonged antimicrobial efficacy with cleaning compositions and other surface treatment compositions are desired.

SUMMARY OF THE INVENTION

According to an aspect, there is provided a surface treatment composition comprising a surface treatment agent; and an antimicrobial mixture comprising oxidizable antimicrobial particles distributed throughout a film-forming agent.

In one embodiment, the oxidizable antimicrobial particles are nanoparticles selected from the group consisting of silver, copper, zinc, gold, and combinations thereof.

In one embodiment, the film-forming agent forms a substantially transparent film on the surface to be treated.

According to another aspect, there is provided a surface treatment composition comprising a transient component comprising a surface treatment agent; and a residual component carried by the transient component for forming a film on a surface that comprises oxidizable antimicrobial particles distributed throughout.

According to another aspect, there is provided a surface treatment composition comprising a residual component for forming, on a treated surface, a film that comprises oxidizable antimicrobial particles distributed throughout; and a transient component carrying the residual component, wherein the film remains on the treated surface in the event that the transient component is removed.

According to another aspect, there is provided a method of use of an antimicrobial mixture in a surface cleaning composition, the antimicrobial mixture comprising oxidizable antimicrobial particles distributed throughout a film-forming agent, the method comprising combining the antimicrobial mixture with a surface cleaning agent and applying the resultant composition to a surface.

According to another aspect, there is provided a surface cleaning composition incorporating oxidizable antimicrobial particles distributed throughout a film-forming agent.

According to another aspect, there is provided a liquid-based cleaning composition incorporating oxidizable antimicrobial particles distributed throughout a film-forming agent.

According to another aspect, there is provided a liquid-based cleaning composition for both cleaning and leaving a residual film on a surface, the residual film incorporating oxidizable antimicrobial particles distributed throughout.

According to another aspect, there is provided a liquid-based surface treatment composition for both cleaning and leaving a residual film on a surface, the residual film incorporating oxidizable antimicrobial particles distributed throughout.

According to another aspect, there is provided a film-forming agent having copper and silver nanoparticles distributed throughout.

According to another aspect, there is provided a textile to which is bonded a film incorporating oxidizable antimicrobial particles distributed throughout.

According to another aspect, there is provided a printable composition comprising a film-forming agent incorporating oxidizable antimicrobial particles distributed throughout.

According to another aspect, there is provided a surface treatment composition comprising a film-forming agent comprising an acrylic polymer emulsion; copper and silver nanoparticles distributed throughout the film-forming agent; and a surface treatment agent comprising water, surfactant, citrus terpenes and isopropyl alcohol.

According to another aspect, there is provided a surface treatment composition comprising: a film-forming agent comprising a silicone emulsion; copper and silver nanoparticles distributed throughout the film-forming agent; and a surface treatment agent comprising paraffin wax, polyethylene wax, citrus terpenes, dimethyl ethanol amine, and a de-foaming agent.

According to another aspect, there is provided a surface treatment composition comprising a film-forming agent comprising a polyurethane emulsion; copper and silver nanoparticles distributed throughout the film-forming agent; and a surface treatment agent comprising silicone, polyethylene wax, paraffin wax, and a de-foaming agent.

The compositions provided herein form a thin solid film that binds to a target surface. Oxidizable antimicrobial particles are distributed throughout the film. The oxidizable antimicrobial particles continue to produce new ions for interfering with biological processes of proximate bacteria and fungi. Furthermore, the oxidizable antimicrobial particles do not require ion exchange conditions in order to produce ions that are harmful to disease-causing bacteria and the like. Furthermore, because the oxidizable antimicrobial particles are distributed throughout the film, antimicrobial activity at the surface continues for as long as some of the film remains on the surface. Thus, even if some oxidizable antimicrobial particles are carried away from the surface along with parts of the film that are gradually worn away over time due to abrasion or the like, other oxidizable antimicrobial particles will remain along with remainder of the film.

BRIEF DESCRIPTION OF THE DRAWING

Embodiments of the invention will now be described with reference to the appended drawings in which.

DETAILED DESCRIPTION

Figure 1:
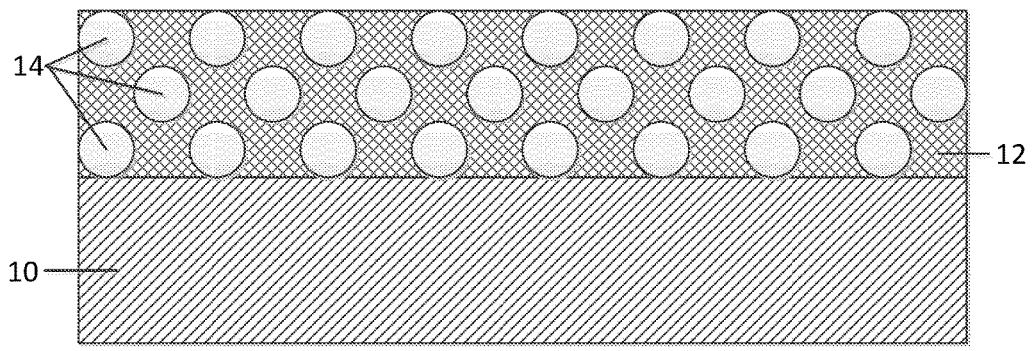
FIG. 1 depicts a surface upon which a film having oxidizable antimicrobial particles distributed throughout has been formed.

Turning now to FIG. 1, there is shown a surface 10 upon which a thin solid film 12 containing oxidizable antimicrobial particles 14 distributed throughout has been formed. The film 12 binds to surface 10 and the oxidizable antimicrobial particles 14 thereby remain associated with surface 10 available as an antimicrobial as long as there remains on the surface some film 12. Surface 10 may be a floor, a table, a doorknob, a sink, a faucet handle, a container, a textile, a fabric or some other surface that is desired to be treated.

Figure 2:
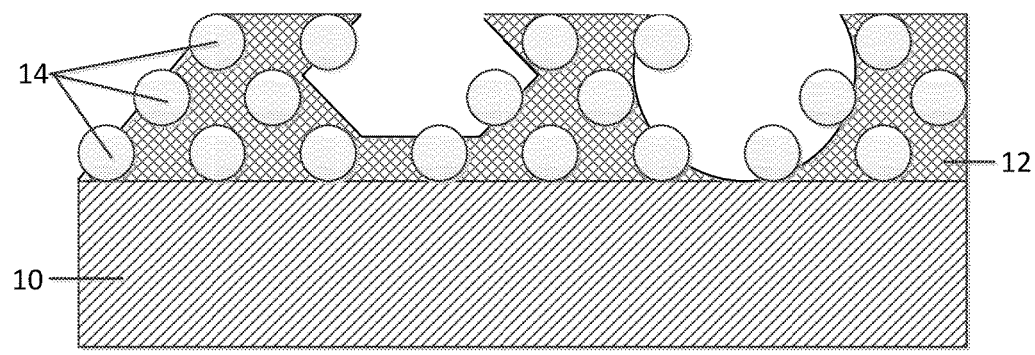
FIG. 2 depicts the film having been partially worn away due to abrasion.

FIG. 2 depicts the film 12, at some time after treatment, having been partially worn away due to abrasion occurring during normal use of surface 10. It can be seen that, despite the abrasion having caused the removal from the surface of several oxidizable antimicrobial particles along with portions of the film 12, the same abrasion has also resulted in exposure of other oxidizable antimicrobial particles that can provide continue to provide antimicrobial function. The amount of time that the oxidizable antimicrobial particles 14 can be effective at the surface 10 corresponds to the amount of time that the film 12 containing the particles can remain bonded to the surface 10. Thus, the greater the extent of the abrasion, the faster the film 12 will deplete, accordingly depleting the numbers of oxidizable antimicrobial particles 14. Similarly, if there is no or very little abrasion, the slower the film 12 will deplete, and the numbers of oxidizable antimicrobial particles 14 will accordingly remain higher for a longer period of time. Because the oxidizable antimicrobial particles 14 themselves continuously produce antimicrobial ions, antimicrobial interference persists as long as the oxidizable antimicrobial particles 14 remain bonded by the film 12 to the surface 10.

It will be understood that FIGS. 1 and 2 are cross-sectional drawings depicting a thin slice of the surface 10, the film 12 and the oxidizable antimicrobial particles 14 distributed uniformly throughout as is preferred. It will be understood that oxidizable antimicrobial particles 14 may be non-uniformly distributed throughout, while still providing prolonged antimicrobial benefits. It will also be understood that the abrasions and pits created in the film 12 over time may have many different shapes and sizes. It is even possible that such abrasions/pits may be made deeply, such that they extend into surface 10 fully removing a section of film 12 and the oxidizable antimicrobial particles 14 distributed in the section. It will be understood that subsequent application of a film-forming material for producing a film 12 will cause the film to form along the surfaces of the abrasions/pits in the surface 10 to provide antimicrobial action therein.

According to the invention the film 12, along with the oxidizable antimicrobial particles 14 distributed throughout, is formed on surface 10 by application to surface 10 of a surface treatment composition. The surface treatment composition includes a surface treatment agent and an antimicrobial mixture comprising oxidizable antimicrobial particles distributed throughout a film-forming agent.

Cleaner

In an embodiment, the oxidizable antimicrobial particles 14 comprise both silver and copper nanoparticles in ratio of 1:30 by weight. Variations are possible. The copper and silver nanoparticles have an average diameter of about 100 nanometers, though variations are possible. It is preferred that the nanoparticles have a weight and surface area that enables the nanoparticles to remain substantially suspended within the surface treatment composition after preparation so as to remain distributed throughout.

In this embodiment, the film-forming agent is an acrylic polymer emulsion that, when applied to a hard, smooth surface such as a metal table, ceramic sink or metal faucet forms a thin, hard, durable acrylic film. During preparation of the antimicrobial mixture a pre-mixture having 0.2% by weight copper nanoparticles, 6% by weight silver nanoparticles and 93.8% by weight water is prepared. The pre-mixture is agitated to distribute the nanoparticles throughout the water, and is then combined with the acrylic polymer emulsion. This combination is agitated thereby to result in the film-forming agent with the oxidizable antimicrobial particles distributed throughout.

In this embodiment, the surface treatment agent is a cleaner that serves also as a transient component of the surface treatment composition that carries the film-forming agent. The surface treatment agent comprises water, surfactant, citrus terpenes, and isopropyl alcohol. The surface treatment agent and the film-forming agent with oxidizable antimicrobial particles distributed throughout are then combined to provide an amount of antimicrobial particles in the composition to produce an antimicrobially-effective amount of oxidizable antimicrobial particles distributed throughout a resultant film.

The cleaner in this embodiment is referred to as a transient component of the surface treatment composition because, after the cleaner has dealt with stains and soiling and disinfection at the surface, it can be removed entirely for example by wiping away. The film-forming agent by comparison is the residual component of the surface treatment composition because it forms a film that remains bonded to a surface even after the cleaner is entirely removed. In this embodiment, the film-forming agent leaves a thin, solid, substantially transparent hard film on the surface.

It is preferred that there be a nanoparticle concentration in the surface treatment composition of about 150 ppm silver nanoparticles (0.0150%) and 75 ppm copper nanoparticles (0.0075%). Thus, for example, for silver nanoparticles, one could employ a 55 gallon drum, which holds 210 kilograms (kg) of water. If solids are at 3% then this corresponds to 6.3 kg (6300 grams) of solids in the drum. To calculate the silver mass, the product of: 6300 grams×0.0150% equals about 1 grams of silver per drum. At about 30% silver by weight, one adds about 3.3 grams of pre-mixture to get 1 gram of silver in the drum.

Higher solids percentage could be calculated proportionally, for example, 30% solids would require 33 grams of pre-mixture per 55 gallon drum.

It will be understood that the oxidizable antimicrobial particles 14 may be of different types, having different sizes and various relative concentrations. The oxidizable antimicrobial particles 14 are referred to as such because these particles, in ionized form, interact with thiol containing proteins and DNA thereby preventing the normal biological functions of bacterial or fungal cells.

While, in this embodiment, the oxidizable antimicrobial particles are silver and copper nanoparticles, it will be appreciated that other metal nanoparticles, such as zinc, titanium, gold and combinations of zinc, titanium, gold, copper and silver or other materials may be employed as alternatives or in some combination.

Hard Surface Protectant

In an alternative embodiment, the antimicrobial pre-mixture has the same nanoparticle composition as that described above, and the film-forming agent is an acrylic polymer emulsion that, when applied to a hard, smooth surface such as glass, ceramic or the like forms a thin, hard, durable and substantially transparent acrylic film. The pre-mixture is agitated to distribute the nanoparticles throughout the water, and is then combined with the acrylic polymer emulsion. This combination is agitated thereby to result in the film-forming agent with the oxidizable antimicrobial particles distributed throughout.

In this embodiment, the surface treatment agent is as described above, and additionally includes ammonia.

It will be understood that in this embodiment also, the oxidizable antimicrobial particles 14 may be of different types, having different sizes and various relative concentrations. While, in this embodiment, the oxidizable antimicrobial particles are silver and copper nanoparticles, it will be appreciated that other metal nanoparticles, such as zinc, titanium, gold and combinations of zinc, titanium, gold, copper and silver or other materials may be employed as alternatives or in some combination.

Polish and Protectant

In an alternative embodiment, the antimicrobial pre-mixture has the same nanoparticle composition as that described above, and the film-forming agent is a silicone emulsion that, when applied to various surfaces such as wood, vinyl and leather forms a thin, durable and substantially transparent silicone film. The pre-mixture is agitated to distribute the nanoparticles throughout the water, and is then combined with the silicone emulsion. This combination is agitated thereby to result in the film-forming agent with the oxidizable antimicrobial particles distributed throughout.

In this embodiment, the surface treatment agent is both a polishing agent and a protectant. The surface treatment agent comprises paraffin and polyethylene waxes, citrus terpenes, dimethyl ethanol amine (DMEA) as a rewetting agent, and a de-foaming agent. The surface treatment agent and the film-forming agent with oxidizable antimicrobial particles distributed throughout are then combined to provide an amount of antimicrobial particles in the composition to produce an antimicrobially-effective amount of oxidizable antimicrobial particles distributed throughout a resultant film.

It will be understood that in this embodiment also, the oxidizable antimicrobial particles 14 may be of different types, having different sizes and various relative concentrations. While, in this embodiment, the oxidizable antimicrobial particles are silver and copper nanoparticles, it will be appreciated that other metal nanoparticles, such as zinc, titanium, gold and combinations of zinc, titanium, gold, copper and silver or other materials may be employed as alternatives or in some combination.

One or both of the waxes may be present.

Sealant

In an alternative embodiment, the antimicrobial pre-mixture has the same nanoparticle composition as that described above, and the film-forming agent is a polyurethane emulsion that, when applied to uneven or porous surfaces such as wood or concrete produces a durable and substantially transparent film over the surface. The pre-mixture is agitated to distribute the nanoparticles throughout the water, and is then combined with the polyurethane emulsion. This combination is agitated thereby to result in the film-forming agent with the oxidizable antimicrobial particles distributed throughout.

In this embodiment, the surface treatment agent is a sealant. The surface treatment agent comprises silicone, polyethylene wax, paraffin wax, and a de-foaming agent. The surface treatment agent and the film-forming agent with oxidizable antimicrobial particles distributed throughout are then combined to provide an amount of antimicrobial particles in the composition to produce an antimicrobially-effective amount of oxidizable antimicrobial particles distributed throughout a resultant film.

It will be understood that in this embodiment also, the oxidizable antimicrobial particles 14 may be of different types, having different sizes and various relative concentrations. While, in this embodiment, the oxidizable antimicrobial particles are silver and copper nanoparticles, it will be appreciated that other metal nanoparticles, such as zinc, titanium, gold and combinations of zinc, titanium, gold, copper and silver or other materials may be employed as alternatives or in some combination.

One or both of the waxes may be present.

Printed Coatings

It has been found that a composition made by combining a film-forming agent such as acrylic polymer, a urethane emulsion or a colloidal-based coating with oxidizable antimicrobial particles such as described above can produces substantial benefits in providing antimicrobial and antifungal protection for packages. Advantageously, coatings for packaging including these film-forming agents with oxidizable antimicrobial nanoparticles distributed throughout along with waxes, de-foaming agents and amines, can be easily integrated into the printing process for product packaging, such that costs of integration of antimicrobial protection can thereby be kept low. Substantial antimicrobial and antifungal benefits would be realized in a retail environment. For example, the antimicrobial benefits of the compositions described above are advantageous when used with packaging containing a cough medicine were coated as described above, as consumers handling such packaging when considering it for purchase may leave behind disease-causing microbes.

Textiles

The dyeing of yarn and textiles is done with a solution containing pigments and particular chemical materials depending on the type of fibers being dyed. For example, acrylic fibers are dyed with basic dyes. Nylon, wool and silk are dyed with acid dyes. Polyester is dyed with disperse dyes. Cotton is dyed with a range of dye types, including vat dyes, and modern synthetic dyes). During the dye process the nanoparticles form a chemical bond with fiber molecules.

Tests Conducted

Cleaner:

A pre-saturated or impregnated towelette was used to wipe hard surfaces contaminated with *Staphylococcus epidermidis* (ATCC #12228) and *Escherichia coli* (ATCC#8739) respectively. Wiped surfaces showed a reduction of 99.85% against *S. epidermidis* and a reduction of 99.72% against *E. coli* after twenty-four (24) hours relative to unwiped surfaces (control).

Hard Surface Protectant:

Testing was conducted on laminated writing shelves contaminated with *Staphylococcus epidermidis* (ATCC #12228). Treated surfaces showed reductions of 94.4% and 80.4% against *S. epidermidis* after twenty-four (24) hours, while untreated surfaces (control) showed no reduction.

Printed Coatings (Papers):

Medical papers treated with the surface treatment agent were tested against *Escherichia coli* (ATCC25922) and *Pseudomonas aeruginosa* (ATCC27853) respectively. Treated medical papers showed a reduction of 99.99% after twenty-four (24) hours, while non treated medical papers (control) showed no reduction.

Printed Coatings (Cartons):

Cartons of 2.5 cm×2.5 cm area were treated with one layer of the film-forming agent and tested against *Escherichia coli* (ATCC25922) and *Pseudomonas aeruginosa* (ATCC27853) respectively. Treated cartons showed reductions of 99.99% against *E. coli* and *P. aeruginosa* after twenty-four (24) hours, while non-treated cartons (control) showed no reduction.

Textiles:

Textiles in a variety of products were tested: Military cotton socks, Black Acrylic Socks, White Cotton Socks, Tan Cotton Socks, Black Acrylic/Polyester Socks, Green Cotton Socks, Wool Socks, Black Cotton Socks, Yellow Spun Polyester Socks, White Cotton Pillowcase, Green Polyester Knit, Cotton Nylon Headwear, Black Polyester Socks, Black Polyester Fabric, and Military Blue Polyester Shirts. These textiles were tested against *Staphylococcus aureus* (ATCC6538), *Klebsiella Pneumoniae* (ATCC4352), and *C. albicans* (ATCC10231) using a sample size of 48±1 mm diameter containing one layer of the film-forming agent. A reduction of 99.99% was observed all after 0, 15, 30 and 50 washes relative to untreated material.

Textiles such as Blue Mattress Ticking Fabric, Polyester Seat Cover, Shoes Liner and Polyester Yarn showed 99.99% reduction of microbes after twenty-four (24) hours treatment (zero (0) washes) relative to untreated material.

It is to be noted that the textile tests were performed using Letheen Broth developed as a subculture medium for the neutralization of quaternary ammonium compounds and other preservatives in disinfectant testing.

While embodiments described above include copper and silver nanoparticles in combination and a particular ratio, variations are possible. For example, the copper and silver particles may be provided in different ratios, or copper may be provided alone or in combination with other suitable oxidizable antimicrobial particles. Similarly, silver may be provided along or in combination with other suitable oxidizable antimicrobial particles. Other suitable oxidizable antimicrobial particles include particles of metals such as zinc, titanium and gold. Furthermore, while metals of the sort described above tend to readily create antimicrobial ions due to ready loss of electrons, other inorganic materials that work substantially the same way to produce substantially the same result, perhaps with faster or slightly slower emission of such antimicrobial ions, may be employed.

It will also be understood that while circles in the figures depict spherical nanoparticles, nanoparticles of different shapes, such as rods, triangles, spheres, and so forth, may be used.

Although embodiments have been described with reference to the drawings, those of skill in the art will appreciate that variations and modifications may be made without departing from the spirit and scope thereof as defined by the appended claims.

What is claimed is:

1. A surface treatment composition comprising:
   a surface treatment agent; and
   an antimicrobial mixture comprising oxidizable antimicrobial copper and silver nanoparticles distributed throughout a film-forming agent,
   wherein the surface treatment agent comprises a surface cleaning agent,
   wherein the surface cleaning agent comprises water, isopropyl alcohol, surfactant and citrus terpenes.

2. The surface treatment composition of claim 1, wherein the oxidizable antimicrobial nanoparticles are uniformly distributed throughout the film-forming agent.

3. The surface treatment composition of claim 1, wherein the antimicrobial mixture further comprises oxidizable antimicrobial nanoparticles selected from the group consisting of: zinc nanoparticles, titanium nanoparticles, gold nanoparticles, and combinations thereof.

4. The surface treatment composition of claim 1, wherein the nanoparticles comprise a 1:30 ratio by weight of copper nanoparticles to silver nanoparticles.

5. The surface treatment composition of claim 4, wherein the copper nanoparticles have a diameter of about 100 manometers.

6. The surface treatment composition of claim 4, wherein the silver nanoparticles have a diameter of about 100 nanometers.

7. The surface treatment composition of claim 1, wherein the film-forming agent forms a polymeric film on the surface when the surface treatment composition is applied to a surface.

8. The surface treatment composition of claim 7, wherein the film-forming agent comprises acrylic acid.

9. The surface treatment composition of claim 1, wherein the film-forming agent forms a substantially transparent film.

10. The surface treatment composition of claim 1, further comprising:
a transient component comprising the surface treatment agent; and
a residual component comprising the antimicrobial mixture.

11. A surface treatment composition comprising:
a surface treatment agent; and
an antimicrobial mixture comprising oxidizable antimicrobial copper and silver nanoparticles distributed throughout a film-forming agent,
wherein the surface treatment agent comprises at least one of: and a surface polishing agent, a surface protectant.

12. The surface treatment composition of claim 11, wherein the film-forming agent comprises silicone, wherein the silicone further functions as at least one of: a sealant, and a protectant.

13. The surface treatment composition of claim 12, wherein the film-forming agent further comprises a rewetting agent.

14. The surface treatment composition of claim 11, wherein the oxidizable antimicrobial nanoparticles are uniformly distributed throughout the film-forming agent.

15. The surface treatment composition of claim 11, wherein the antimicrobial mixture further comprises oxidizable antimicrobial nanoparticles selected from the group consisting of: zinc nanoparticles, titanium nanoparticles, gold nanoparticles, and combinations thereof.

16. The surface treatment composition of claim 11, wherein the nanoparticles comprise a 1:30 ratio by weight of copper nanoparticles to silver nanoparticles.

17. The surface treatment composition of claim 16, wherein the copper nanoparticles have a diameter of about 100 nanometers.

18. The surface treatment composition of claim 16, wherein the silver nanoparticles have a diameter of about 100 nanometers.

19. The surface treatment composition of claim 11, wherein the film-forming agent forms a polymeric film on the surface when the surface treatment composition is applied to a surface.

20. The surface treatment composition of claim 19, wherein the film-forming agent comprises acrylic acid.

21. The surface treatment composition of claim 11, wherein the film-forming agent forms a substantially transparent film.

22. The surface treatment composition of claim 11, further comprising:
a transient component comprising the surface treatment agent; and
a residual component comprising the antimicrobial mixture.

23. A surface treatment composition comprising:
a surface treatment agent; and
an antimicrobial mixture comprising oxidizable antimicrobial copper and silver nanoparticles distributed throughout a film-forming agent,
wherein the surface treatment agent comprises a surface sealant.

24. The surface treatment composition of claim 23, wherein the oxidizable antimicrobial nanoparticles are uniformly distributed throughout the film-forming agent.

25. The surface treatment composition of claim 23, wherein the antimicrobial mixture further comprises oxidizable antimicrobial nanoparticles selected from the group consisting of: zinc nanoparticles, titanium nanoparticles, gold nanoparticles, and combinations thereof.

26. The surface treatment composition of claim 23, wherein the nanoparticles comprise a 1:30 ratio by weight of copper nanoparticles to silver nanoparticles.

27. The surface treatment composition of claim 26, wherein the copper nanoparticles have a diameter of about 100 nanometers.

28. The surface treatment composition of claim 26, wherein the silver nanoparticles have a diameter of about 100 nanometers.

29. The surface treatment composition of claim 23, wherein the film-forming agent forms a polymeric film on the surface when the surface treatment composition is applied to a surface.

30. The surface treatment composition of claim 29, wherein the film-forming agent comprises acrylic acid.

31. The surface treatment composition of claim 23, wherein the film-forming agent forms a substantially transparent film.

32. The surface treatment composition of claim 23, further comprising:
a transient component comprising the surface treatment agent; and
a residual component comprising the antimicrobial mixture.

* * * * *

UNITED STATES PATENT AND TRADEMARK OFFICE
CERTIFICATE OF CORRECTION

PATENT NO.        : 10,271,545 B2
APPLICATION NO.   : 15/043762
DATED             : April 30, 2019
INVENTOR(S)       : Jeffrey M. Lord et al.

It is certified that error appears in the above-identified patent and that said Letters Patent is hereby corrected as shown below:

In the Claims

Column 8, Line 58 Claim 5 "manometers" should be "nanometers"

Column 9, Line 16 Claim 11 "and a surface polishing agent, a surface protectant" should be "a surface polishing agent, and a surface protectant"

Signed and Sealed this
Third Day of September, 2019

Andrei Iancu
*Director of the United States Patent and Trademark Office*